United States Patent
Agrawal et al.

(10) Patent No.: US 10,830,747 B2
(45) Date of Patent: Nov. 10, 2020

(54) SYSTEM AND METHOD FOR PREDICTING FATIGUE STRENGTH OF ALLOYS

(71) Applicant: Northwestern University, Evanston, IL (US)

(72) Inventors: Ankit Agrawal, Evanston, IL (US); Alok Choudhary, Chicago, IL (US)

(73) Assignee: Northwestern University, Evanston, IL (US)

( * ) Notice: Subject to any disclaimer, the term of this patent is extended or adjusted under 35 U.S.C. 154(b) by 279 days.

(21) Appl. No.: 15/793,376

(22) Filed: Oct. 25, 2017

(65) Prior Publication Data

US 2018/0113967 A1    Apr. 26, 2018

Related U.S. Application Data

(60) Provisional application No. 62/413,261, filed on Oct. 26, 2016.

(51) Int. Cl.
| | | |
|---|---|---|
| *G01N 33/202* | (2019.01) | |
| *G01N 33/20* | (2019.01) | |
| *G06F 16/2458* | (2019.01) | |
| *G06F 30/20* | (2020.01) | |
| *G01N 33/2022* | (2019.01) | |
| *G01N 33/2025* | (2019.01) | |
| *G01N 33/2028* | (2019.01) | |
| *G06F 30/333* | (2020.01) | |

(52) U.S. Cl.
CPC .......... *G01N 33/202* (2019.01); *G01N 33/20* (2013.01); *G01N 33/2022* (2019.01); *G01N 33/2025* (2019.01); *G01N 33/2028* (2019.01); *G06F 16/2465* (2019.01); *G06F 30/20* (2020.01); *G01N 2203/0073* (2013.01); *G01N 2203/0218* (2013.01); *G01N 2203/0246* (2013.01); *G06F 30/333* (2020.01)

(58) Field of Classification Search
CPC .......... G01N 33/20; G01N 2203/0073; G01N 2203/0246; G01N 33/208–2028; G06F 17/5009; G06F 16/2465
See application file for complete search history.

(56) References Cited

PUBLICATIONS

Agrawal, Ankit et al. "Exploration of data science techniques to predict fatigue strength of steel from composition and processing parameters" Integrating Materials and Manufacturing Innovations 2014, 3:8 http://www.immijournal.com/content/3/1/8. (Year: 2014).*

* cited by examiner

*Primary Examiner* — Paul M. West
(74) *Attorney, Agent, or Firm* — Benesch, Friedlander, Coplan & Aronoff LLP

(57) ABSTRACT

Systems and methods include a predictor module configured to receive an input, e.g., composition parameters and processing parameters. A processor processes the input to predict a material property, e.g., fatigue strength, of an alloy based on the input. The processor outputs the predicted fatigue strength of the alloy for display.

12 Claims, 9 Drawing Sheets

Composition Parameters: — 702

| Parameter | Value |
|---|---|
| Carbon (C) (wt %) (0.17–0.63) | 0.388 |
| Silicon (Si) (wt %) (0.16–2.05) | 0.3 |
| Manganese (Mn) (wt %) (0.37–1.6) | 0.823 |
| Phosphorus (P) (wt %) (0.002–0.031) | 0.016 |
| Sulphur (S) (wt %) (0.003–0.03) | 0.015 |
| Nickel (Ni) (wt %) (0.01–2.78) | 0.517 |
| Chromium (Cr) (wt %) (0.01–1.17) | 0.57 |
| Copper (Cu) (wt %) (0.01–0.26) | 0.068 |
| Molybdenum (Mo) (wt %) (0.00–0.24) | 0.07 |
| Area Proportion of Inclusions Deformed by Plastic Work (0.00–0.13) | 0.05 |
| Area Proportion of inclusions occurring in Discontinuous array (0.00–0.05) | 0.01 |
| Area Proportion of Isolated Inclusions (0.000–0.058) | 0.01 |

Processing Parameters: — 704

| Parameter | Value |
|---|---|
| Normalizing Temperature (°C) (825–930) | 872 |
| Through Hardening Temperature (°C) (30–865) | 850 |
| Through Hardening Time (minutes) (0–30) | 30 |
| Cooling Rate for Through Hardening (°C/hr) (0–24) | 8 |
| Carburization Temperature (°C) (30–930) | 30 |
| Carburization Time (minutes) (0–540) | 0 |
| Diffusion Temperature (°C) (30–903) | 30 |
| Diffusion Time (minutes) (0.0–70.02) | 0 |
| Quenching Media Temperature for Carburization (°C) (30–140) | 30 |
| Tempering Temperature (°C) (30–680) | 550 |
| Tempering Time (minutes) (0–120) | 60 |
| Cooling Rate for Tempering (°C/hr) (0–24) | 24 |
| Reduction Ratio (Ingot to Bar) (240–5530) | 1000 |

Do not have values for all attributes?
Try the calculator with reduced attribute set instead!

FIG. 7

SYSTEM AND METHOD FOR PREDICTING FATIGUE STRENGTH OF ALLOYS

CROSS-REFERENCE TO RELATED APPLICATIONS

This patent application claims the benefit of U.S. Provisional Patent Application No. 62/413,261, filed on Oct. 26, 2016, the entire contents of which is incorporated by reference in its entirety.

STATEMENT OF FEDERALLY FUNDED RESEARCH

This invention was made with government support under FA9550-12-1-0458 awarded by the Air Force Office of Scientific Research and 70NANB14H012 awarded by the National Institute of Standards and Technology (NIST). The government has certain rights in the invention.

BACKGROUND

The field of materials science and engineering can involve conducting experiments and simulations to understand the science of materials in order to discover and engineer new materials. Over the last few years, data generated by experiments and simulations has grown exponentially. In the field of materials science, this has led to the emergence of a new field called materials informatics, which deciphers the processing-structure-property-performance (PSPP) relationships in materials science.

In June 2011, the US government launched the Materials Genome Initiative (MGI) to realize the vision of development of advanced materials necessary for economic security and human well-being. The MGI Strategic Plan released in 2014 identifies data analytics as an objective as part of integrating experiments, computation and theory. MGI-supported efforts and other similar efforts around the world are promoting the availability and accessibility of digital data in materials science.

BRIEF DESCRIPTION OF DRAWINGS

FIG. 7 is a screenshot of an example expanded fatigue strength predictor of the predictor module.

DESCRIPTION

The systems and methods include a predictor module and related systems for predicting a material property, e.g., a field strength, of alloys. For purposes of explanation, the systems and methods are described for predicting a fatigue strength of steel alloys, but other metals may be used. Fatigue strength is a mechanical property of steel and the predictor module can be used to predict other properties too, based on an implementation. In some examples, the fatigue strength of steel alloys is represented by their composition and processing information. In some examples, the PSPP relationships, predicting property of a material given its composition and processing parameters, are built in accordance with observations from the Japan National Institute of Materials Science (NIMS) steel fatigue dataset. Other databases can be used. Modeling techniques, including but not limited to ensemble modeling, can identify models for different attribute sets. In some examples, data-driven feature selection techniques can be used to find a small non-redundant subset of composition and processing attributes for the predictive module. In some examples, the predictive module can be deployed in as an online web-tool, e.g., available at http://info.eecs.northwestern.edu/SteelFatigueStrengthPredictor, or mobile application (example screenshots in FIGS. 6-8).

Figure 1:
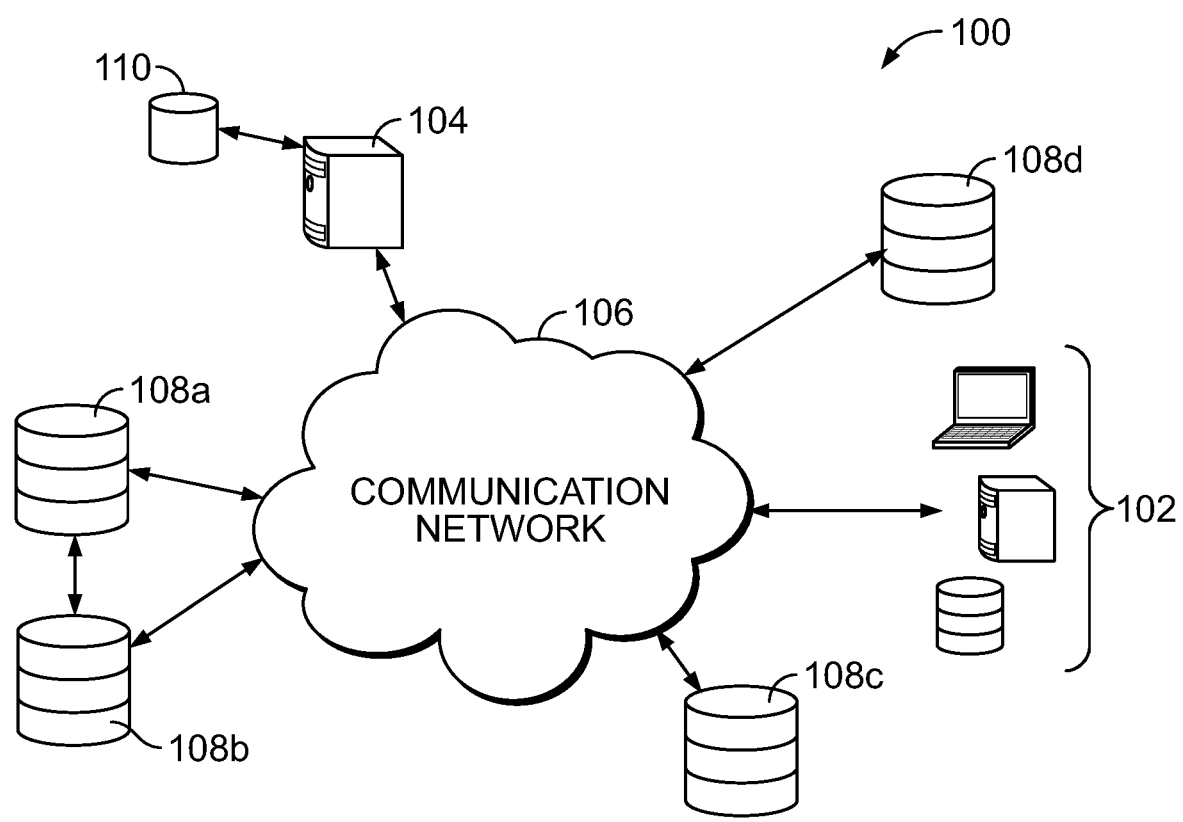
FIG. 1 is a block diagram of an example environment for predicting a fatigue strength of alloys.

FIG. 1 is a block diagram of an example environment 100 for predicting a material property, e.g., a field strength, of alloys, e.g., steel alloys. For the purpose of explanation the field strength is described in terms of a fatigue strength. User devices 102 can communicate with the predictor module 104 via a communication network 106. The user devices 102 can include mobile devices that run an application, e.g., smartphones, tablets, smartwatches, personal digital assistants (PDA's), etc., and/or mobile or desktop devices that can access a portal, e.g., via a web browser, including computers, e.g., desktops, laptops, tablets, etc. For entering and/or viewing information to/from predictor module 104, the user devices 102 can include user interfaces and displays, as described in more detail below. The communication environment 106 can provide wireless and/or wired communications between the user devices 102, predictor module 104 and/or databases 108a-d and 110, including, but not limited to, cellular, Wi-Fi, Bluetooth, Ethernet, public switched telephone network, etc. communications.

The user devices 102 can be used to input composition parameters and/or processing parameters of the alloys to the predictor module 104, and send the parameters to the predictor module 104 which uses to make alloy fatigue strength predictions. The user devices 102 can also receive a predicted fatigue strength of the alloy from the predictor module 104 and display the predicted fatigue strength to users. The predictor module 104 can also connect with one or more databases 108a-b to obtain data used for making the strength predictions, as described in more detail below. In some examples, the databases include the Japan NIMS steel fatigue dataset. Other databases can be used. The predictor module 104 can receive and store data used for the predictions locally in database 110 for processing and/or process the data stored in the databases 108a-d without the need to store is locally. In some examples, the predictor module 104 mines the data stored in the databases 108a-d, e.g., sorts through the datasets to identify patterns and establish relationships to predict alloy strength through data analysis, e.g., based on the composition parameters and/or processing parameters received from the user devices 102.

For purposes of explanation, the predictor module 104 predicts a fatigue strength of an inputted steel alloy, which can help save a cost and time of fatigue testing, and potentially negative consequences of fatigue failures. Fatigue strength can provide important information for design and failure analysis of mechanical components. In some examples, fatigue strength is estimated to account for over 90% of all mechanical failures of structural components. As described in more detail below, in some examples, the predictor module 104 uses only composition attributes and processing attributes to predict strength. In some examples, the predictor module 104 provides a reduced set of non-redundant attributes to require fewer inputs while still providing a determined predictive accuracy. In some examples, the predictor module 104 can be used by materials science and engineering communities to make fast and accurate predictions of the fatigue property of steel or other alloys, which can aid in discovering better steels and other alloys.

Figure 2:
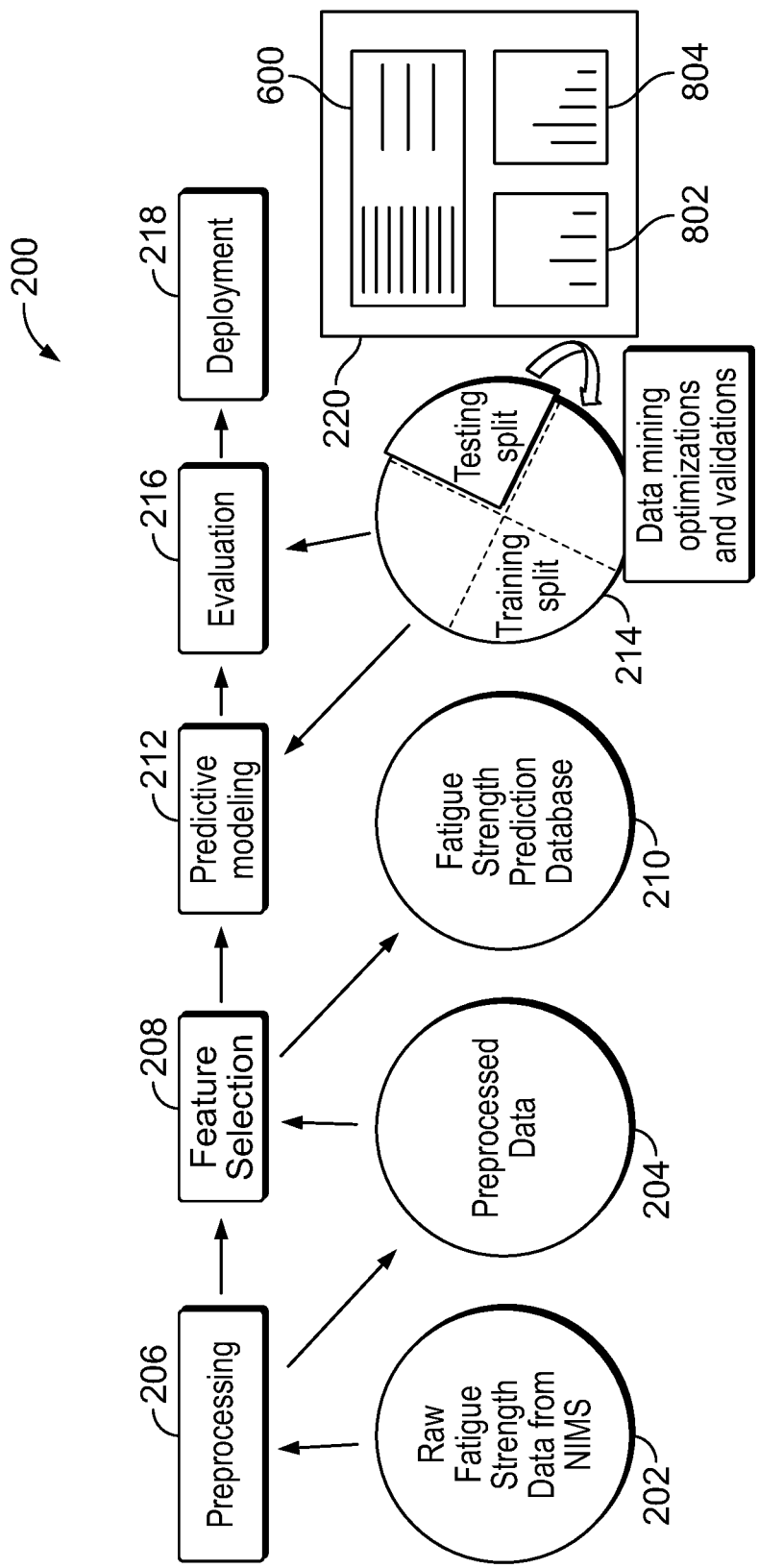
FIG. 2 is a block diagram of an example data mining workflow of the predictor module.

FIG. 2 is a block diagram of an example data mining workflow 200 of the predictor module 104. For the sake of explanation, rotating bending fatigue testing data 202 can be obtained from the databases 108a-d, e.g., a publicly available NIMS MatNavi database. In some examples, the predictor module 104 can preprocess the data (206), e.g., as described in A. Agrawal, P. D. Deshpande, A. Cecen, G. P. Basavarsu, A. N. Choudhary, S. R. Kalidindi, "Exploration of data science techniques to predict fatigue strength of steel from composition and processing parameters," Integrating Materials and Manufacturing Innovation 3 (8), 2014, pp. 1-19. The preprocessed NIMS database includes various steels, e.g., composition and processing parameters as well as corresponding fatigue strength. The NIMS database can be data mined to build predictive models using various data mining techniques. The predictive models can be stored along with the predictor module 104, which accepts input parameters of a given steel from the user device 102. Inputted parameters can include, but are not limited to, steel composition/processing parameters for making prediction of fatigue strength of the given steel. The input parameters for the given steels are generally different from the steels stored in the NIMS database. The predictor module 104 can use the stored models to determine the predicted fatigue strength for the inputted steel parameters, and then display the predicted fatigue strength to the user device 102.

In some examples, the predictor module 104 can perform feature selection to identify a reduced, non-redundant subset of attributes to be used as inputs for prediction, so that the user devices 102 do not have to enter a lot of values (208). The fatigue strength prediction parameters 210 can be stored in database 110. The predictor module 104 can use the prediction parameters 210 for predictive modeling (212). The predictor module 104 can use learning techniques on dataset 214 to learn predictive models for fatigue strength. The predictor module 104 can evaluate the predictive models 212 using validation techniques (216), and deploy the accurate models to the user devices 102, e.g., in an online web-tool and/or mobile application that can predict the fatigue strength of arbitrary inputted compositions and processing parameters (218).

In some examples, the predictor module 104 accesses the fatigue dataset for steel from the Japan NIMS MatNavi to obtain the raw fatigue strength data 202. The Japan NIMS MatNavi is a large database with details on composition, mill product (upstream) features and subsequent processing (heat treatment) parameters. The Japan NIMS MatNavi includes information on carbon and low-alloy steels, carburizing steels and spring steels, for example. Apart from composition and processing details, the Japan NIMS MatNavi also includes data on mechanical properties of steels, e.g., rotating bending fatigue strength at 10' cycles at room temperature conditions. Fatigue strength includes the highest stress that a material can withstand for a given number of cycles without breaking, and is thus can be an important property of steel for industrial use. The features in the NIMS dataset can be categorized into the following: chemical composition—% C, % Si, % Mn, % P, % S, % Ni, % Cr, % Cu, % Mo (all in wt. %); upstream processing details, e.g., ingot size, reduction ratio, non-metallic inclusions; heat treatment conditions, e.g., temperature, time and other process conditions for normalizing, through-hardening, carburizing, quenching and tempering processes; and mechanical property, e.g., fatigue strength (MPa).

The raw dataset 202 from NIMS includes multiple grades of steel and in some records, some of the heat treatment processing steps do not exist. This is because different specimens can be subjected to different processing routes where some processing steps may not have occurred. To make a coherent database, the predictor module 104 can include the processes in the data, e.g., normalization, through hardening, carburization, quenching, and tempering. For the cases where a given process did not take place, the predictor module 104 can set a corresponding time variable to zero and set the corresponding temperature to the austenization temperature or the average of rest of the data where the process exists. The preprocessed data 204 can also be made publicly available as supplementary to the raw data 202.

In some examples, the preprocessed data 204 can include hundreds of instances/rows and dozens of features/columns (composition and processing parameters), and a single target property (fatigue strength). The details of the attributes can include: C—% Carbon, Si—% Silicon, Mn—% Manganese, P—% Phosphorus, S—% Sulphur, Ni—% Nickel, Cr—% Chromium, Cu—% Copper, Mo—% Molybdenum, NT—Normalizing Temperature, THT—Through Hardening Temperature, THt—Through Hardening Time, THQCr—Cooling Rate for Through Hardening, CT—Carburization Temperature, Ct—Carburization Time, DT—Diffusion Temperature, Dt—Diffusion time, QmT—Quenching Media Temperature (for Carburization), TT—Tempering Temperature, Tt—Tempering Time, TCr—Cooling Rate for Tempering, RedRatio—Reduction Ratio (Ingot to Bar), dA—Area Proportion of Inclusions Deformed by Plastic Work, dB—Area Proportion of Inclusions Occurring in Discontinuous Array, dC—Area Proportion of Isolated Inclusions, and Fatigue—Rotating Bending Fatigue Strength (e.g., $10^7$ Cycles).

In some examples, the predictor module 104 can use a correlation feature selection (CFS) method for feature ranking. CFS is used to identify a subset of features highly correlated with the class variable and weakly correlated amongst them. The predictor module 104 can use CFS in conjunction with a best first search to find a subset S with best average merit, which is given by:

$$\text{Merit}_S = \frac{n.\overline{r_{fo}}}{\sqrt{n + n(n-1).\overline{r_{ff}}}}$$

where n is the number of features in S, $\overline{r_{fo}}$ is the average value of feature-outcome correlations, and $\overline{r_{ff}}$ is the average value of all feature-feature correlations.

The predictive modeling 212 can include regression schemes, including both direct application of regression techniques and constructing their ensembles using various ensembling techniques, including, but not limited to, one or more of 1) linear regression, 2) nearest-neighbor (IBk), 3) nearest-neighbor (KStar), 4) artificial neural networks, 5) Gaussian process, 6) support vector machines, 7) decision tables, 8) decision stumps, 9) M5 model trees, 10) random trees, 11) reduced error pruning tree, 12) random forest, 13) additive regression, 14) bagging, 15) random committee, 16) random subspace, 17) rotations forest and/or 18) voting. Linear regression represents a regression that is linear in the unknown parameters used in the fit. Least squares fitting of lines and polynomials are both forms of linear regression. Nearest-neighbor (IBk), also known as instance-based model, uses normalized Euclidean distance to find the training instance closest to the given test instance, and predicts the same target value as this training instance. If multiple instances have the same (smallest) distance to the test instance, the first one found is used. It eliminates the need for building models and supports adding new instances to the training database dynamically. Nearest-neighbor (KStar) is another type of nearest-neighbor model that uses an entropy-based distance function instead of Euclidean distance.

Artificial neural networks (ANNs) are networks of interconnected artificial neurons, and are used for non-linear statistical data modeling to model complex relationships between inputs and outputs. The network includes a hidden layer of multiple artificial neurons connected to the inputs and outputs with different edge weights. The internal edge weights are learnt during the training process using techniques like back propagation. In some examples, the predictor module 104 uses multilayer perceptron (MLP) for regression with one hidden layer. A Gaussian Process generates data located throughout some domain such that any finite subset of the range follows a multivariate Gaussian distribution, and uses that distribution to make predictions. Support vector machines (SVMs) are based on the Structural Risk Minimization (SRM) principle from statistical learning theory. In some examples, the predictor module 104 uses SVMs for regression. SVMs attempt to perform modeling by constructing hyperplanes in a multidimensional space that separates the instances according to the target variable. SMVs support both classification and regression tasks and can handle multiple continuous and nominal variables.

Decision tables construct rules involving different combinations of attributes, which are selected using an attribute selection search method. A decision stump is a weak tree-based machine learning model including a single-level decision tree with a categorical or numeric class label. Decision stumps are usually used in ensemble machine learning techniques. M5 Model Trees are a reconstruction of Quinlan's M5 algorithm for inducing trees of regression models, which combines a conventional decision tree with the option of linear regression functions at the nodes. M5 Model Trees try to partition the training data using a decision tree induction algorithm by trying to minimize the intra-subset variation in the class values down each branch, followed by back pruning and smoothing, which increases prediction performance. M5 Model Trees also uses the techniques used in CART to effectively deal with enumerated attributes and missing values. Random Tree is a decision tree model that considers a randomly chosen subset of attributes at each node. The number of attributes chosen are, in general, significantly less than the total number of attributes. Random trees are usually used as building blocks for random forests, which, in general, has been found to improve prediction performance. Reduced error pruning tree, known as REPTree, is an implementation of a fast decision tree learner, which builds a decision/regression tree using information gain/variance and prunes it using reduced-error pruning to avoid over-fitting. Part of the training data is withheld from decision tree construction as a pruning set and is subsequently used for pruning. At each internal node in the tree, an error rate is identified by propagating the errors upwards from the leaf nodes. This is compared to the error rate if that internal node was replaced by a leaf node with the average value of the target attribute in that node. If it results in a reduction of error, then the subtree below the node can be pruned, and the node with the highest scope of reducing error is pruned. The random forest model includes multiple decision trees. In that sense, it is an ensemble of random trees. The final prediction of an instance in a random forest is given by the average of the predictions from the individual trees. In many cases, the random forest is known to produce robust and accurate predictions, along with the ability to handle a very large number of input variables, while also being relatively robust to over-fitting.

Additive regression is a meta learner that enhances the performance of a regression base classifier. Each iteration fits a model to the residuals left by the classifier on the previous iteration. The predictions of each of the learners are added together to get the overall prediction. Bagging is an ensemble learning algorithm to improve the stability of classification and regression algorithms by reducing variance. Bagging is usually applied to decision tree models to boost their performance. It involves generating a number of new training sets, called bootstrap modules, from the original set by sampling uniformly with replacement. The bootstrap modules are then used to generate models whose predictions are averaged to generate the final prediction. Bagging has been shown to work better with decision trees than with linear models. Random Committee is a technique for building an ensemble of randomizable base models. Each base model is built using a different random seed but uses the exact same data. The final prediction is a simple average of the individual predictions. The random subspace ensembling technique constructs a decision tree based model consisting of multiple trees, which are constructed systematically by pseudo-randomly selecting subsets of features, trying to achieve a balance between overfitting and achieving maximum accuracy. It maintains highest accuracy on training data and improves on generalization accuracy as it grows in complexity.

Rotation Forest is a method for generating model ensembles based on feature extraction, which can work both with classification and regression base learners. Training data for the base modeling technique is created by applying Principal Component Analysis (PCA) to K subsets of the feature set, followed by K axis rotations to form the new features for the base learner, to encourage simultaneously individual accuracy and diversity within the ensemble. Voting is a popular ensemble technique for combining multiple classifiers. Ensemble classifiers using voting may outperform the individual classifiers in certain cases. The predictor module 104 can combine multiple classifiers by using the average of predictions generated by each model, although the predictions can be combined in other ways, such as taking the maximum, minimum, median, etc.

In some examples, the predictor module 104 obtains different modeling configurations using the above techniques as follows. For example, the predictor module 104 uses techniques 1-12 on the training data to get predictive models. The five ensembling techniques, techniques 13-17, work in conjunction with a base modeling technique. In some examples, the predictor module 104 excluded the two nearest-neighbor models, Gaussian process, SVM, decision table, and random forest models while ensembling for one or more of the following reasons: large model size, large training/testing time, low accuracy, already an ensemble model. Of five ensemble methods, random committee works with randomizable base models, e.g., which use a random seed to build a model. Three of the remaining direct modeling techniques fulfill that criterion, which are multilayer perceptron, random tree, and reduced error pruning trees. Further, the predictor module 104 can identify a set of best performing models from the above analysis whose performance are not statistically distinguishable at p=0.05, and an ensemble voting model (technique 18) that averages the predictions from the best performing models to generate the final prediction.

The predictor module 104 can use quantitative assessments of the degree to how close the models predict the experimental fatigue strength to evaluate the models' predictive performance (216). Metrics used for this purpose include the coefficient of correlation (R), explained variance ($R^2$), Mean Absolute Error (MAE), Root Mean Squared Error (RAISE), Relative Absolute Error (RAE), and Root Relative Squared Error (RRSE). Formulae of these evaluation criteria are as follows:

$$R = \frac{\sum_{i=1}^{N}(y_i - \bar{y})(\hat{y}_i - \bar{\hat{y}})}{\sqrt{\sum_{i=1}^{N}(y_i - \bar{y})^2 \sum_{i=1}^{N}(\hat{y}_i - \bar{\hat{y}})^2}} \quad (1)$$

$$MAE = \bar{e} = \frac{1}{N}\sum_N |y - \hat{y}| \quad (2)$$

$$RMSE = \sqrt{\frac{1}{N}\sum_N (y - \hat{y})^2} \quad (3)$$

$$RAE = \frac{\sum_N |y - \hat{y}|}{\sum_N |y - \bar{y}|} \quad (4)$$

$$RRSE = \sqrt{\frac{\sum_N (y - \hat{y})^2}{\sum_N (y - \bar{y})^2}} \quad (5)$$

where y denotes the actual fatigue strength (MPa), $\hat{y}$ denotes the predicted fatigue strength (MPa), $\bar{y}$ denotes the average fatigue strength across the dataset, and N is the number of instances in the dataset.

In some examples, the predictor module 104 can use a cross validation setting to evaluate the models, which randomly divides the dataset 214 into multiple parts, e.g., 9 parts as training set and 1 part as the test set, and repeats the process a determined number of times with different test sets before aggregating the results together. Therefore, each labeled instance in the steel fatigue strength prediction database is tested once by a model that did not see it while training. The predictor module 104 can repeat the entire process a determined number of times to aid in statistical significance testing. The predictor module 104 determined optimizations and validations can be used to determine inputs for the input screen 600 (e.g., FIG. 6). Graphs of example histograms of steel fatigue strength data 802 and prediction errors 804 of the fatigue strength predictor of the predictor module 104 (e.g., FIG. 8).

Table 1 is an example comparison of different techniques with 10-fold cross-validation setting using all attributes (table sorted by MAE, where example best accuracy numbers are boldfaced that were statistically not distinguishable at p=0.05, and modeling techniques used in final Voting model also are boldfaced).

TABLE 1

| Modeling Scheme | R | $R^2$ | MAE (MPa) | RMSE (MPa) | RAE (%) | RRSE (%) | TrainTime (s) | TestTime (s) | ModelSize (bytes) |
|---|---|---|---|---|---|---|---|---|---|
| RotationForest_M5 | 0.9900 | 0.9801 | 18.74 | 26.50 | 14.76 | 14.44 | 1.1058 | 0.0094 | 716215 |
| RotationForest_MLP | 0.9894 | 0.9789 | 18.97 | 27.00 | 15.00 | 14.76 | 3.4866 | 0.0102 | 664851 |
| Bagging_MLP | 0.9895 | 0.9791 | 18.97 | 27.03 | 14.99 | 14.78 | 3.0486 | 0.0009 | 99700 |
| AdditiveRegression_M5 | 0.9897 | 0.9795 | 19.05 | 26.66 | 15.01 | 14.54 | 0.3996 | 0.0003 | 44210 |
| Bagging_M5 | 0.9890 | 0.9781 | 19.36 | 27.96 | 15.23 | 15.21 | 0.8039 | 0.0008 | 264058 |
| M5 ModelTrees | 0.9893 | 0.9787 | 19.64 | 27.46 | 15.45 | 14.94 | 0.0885 | 0.0001 | 19684 |
| NeuralNetworks (MLP) | 0.9881 | 0.9763 | 19.89 | 28.41 | 15.72 | 15.56 | 0.3652 | 0.0002 | 13616 |
| RandomCommittee_MLP | 0.9877 | 0.9756 | 20.37 | 29.14 | 16.05 | 15.84 | 3.0811 | 0.0010 | 99424 |
| AdditiveRegression_MLP | 0.9851 | 0.9704 | 20.94 | 32.27 | 16.49 | 17.56 | 3.5265 | 0.0009 | 99476 |
| RandomCommittee_REPTree | 0.9874 | 0.9750 | 21.39 | 29.48 | 16.86 | 16.09 | 0.0637 | 0.0003 | 83087 |
| Bagging_REPTree | 0.9872 | 0.9746 | 21.44 | 29.90 | 16.88 | 16.29 | 0.0597 | 0.0002 | 103283 |
| RotationForest_REPTree | 0.9871 | 0.9744 | 21.82 | 30.06 | 17.20 | 16.39 | 0.2026 | 0.0086 | 653435 |
| RotationForest_RandomTree | 0.9866 | 0.9734 | 22.25 | 30.58 | 17.57 | 16.69 | 0.1698 | 0.0088 | 941446 |
| RandomForest | 0.9875 | 0.9752 | 22.28 | 29.43 | 17.59 | 16.08 | 0.2594 | 0.0025 | 2762888 |
| RandomCommittee_RandomTree | 0.9858 | 0.9718 | 23.59 | 31.42 | 18.65 | 17.18 | 0.0416 | 0.0003 | 430293 |
| Bagging_RandomTree | 0.9853 | 0.9708 | 23.96 | 31.78 | 18.94 | 17.38 | 0.0323 | 0.0003 | 275199 |
| SVM | 0.9816 | 0.9635 | 24.34 | 36.65 | 19.12 | 19.90 | 0.3355 | 0.0001 | 110816 |
| RotationForest_LinearRegression | 0.9834 | 0.9671 | 24.62 | 34.26 | 19.37 | 18.62 | 0.1698 | 0.0088 | 610462 |
| Bagging_LinearRegression | 0.9832 | 0.9667 | 24.69 | 34.48 | 19.42 | 18.73 | 0.0341 | 0.0003 | 43911 |
| AdditiveRegression_REPTree | 0.9797 | 0.9598 | 24.71 | 35.70 | 19.43 | 19.39 | 0.0127 | 0.0001 | 13277 |
| REPTree | 0.9812 | 0.9628 | 24.87 | 35.17 | 19.59 | 19.18 | 0.0064 | 0.0001 | 10449 |
| AdditiveRegression_LinearRegression | 0.9830 | 0.9663 | 24.99 | 34.64 | 19.66 | 18.84 | 0.0117 | 0.0001 | 12111 |
| LinearRegression | 0.9830 | 0.9663 | 24.99 | 34.64 | 19.66 | 18.83 | 0.0031 | 0.0001 | 7598 |
| RandomSubSpace_REPTree | 0.9829 | 0.9661 | 26.48 | 34.18 | 20.93 | 18.70 | 0.0388 | 0.0003 | 89933 |
| RandomSubSpace_MLP | 0.9814 | 0.9631 | 27.25 | 36.06 | 21.49 | 19.67 | 1.5278 | 0.0010 | 100764 |
| RandomSubSpace_M5 | 0.9821 | 0.9645 | 27.45 | 35.67 | 21.70 | 19.51 | 0.6407 | 0.0008 | 158759 |
| RandomSubSpace_RandomTree | 0.9768 | 0.9541 | 31.19 | 38.65 | 24.72 | 21.22 | 0.0359 | 0.0005 | 349143 |

TABLE 1-continued

| Modeling Scheme | R | $R^2$ | MAE (MPa) | RMSE (MPa) | RAE (%) | RRSE (%) | TrainTime (s) | TestTime (s) | ModelSize (bytes) |
|---|---|---|---|---|---|---|---|---|---|
| AdditiveRegression_DecisionStump | 0.9663 | 0.9337 | 34.42 | 47.87 | 27.12 | 26.13 | 0.0156 | 0.0001 | 4194 |
| RandomTree | 0.9708 | 0.9425 | 34.82 | 44.35 | 27.55 | 24.33 | 0.0041 | 0.0001 | 45445 |
| AdditiveRegression_RandomTree | 0.9715 | 0.9438 | 34.85 | 43.68 | 27.60 | 23.96 | 0.0104 | 0.0001 | 76641 |
| GaussianProcess | 0.9670 | 0.9351 | 34.86 | 48.11 | 27.35 | 26.13 | 0.0846 | 0.0740 | 732187 |
| RandomSubSpace_LinearRegression | 0.9660 | 0.9332 | 36.41 | 49.40 | 28.66 | 26.92 | 0.0191 | 0.0005 | 54937 |
| DecisionTable | 0.9445 | 0.8921 | 37.21 | 58.47 | 29.34 | 31.81 | 0.0511 | 0.0002 | 24944 |
| NearestNeighbor_Kstar | 0.9610 | 0.9235 | 40.37 | 49.81 | 32.01 | 27.36 | 0.0001 | 0.1965 | 110615 |
| NearestNeighbor_Ibk | 0.9539 | 0.9099 | 47.86 | 55.65 | 37.92 | 30.39 | 0.0001 | 0.0037 | 97573 |
| RotationForest_DecisionStump | 0.8622 | 0.7434 | 70.67 | 91.81 | 55.60 | 50.15 | 0.1494 | 0.0085 | 572252 |
| RandomSubSpace_DecisionStump | 0.8402 | 0.7059 | 73.13 | 97.49 | 57.55 | 53.31 | 0.0106 | 0.0002 | 24493 |
| DecisionStump | 0.8402 | 0.7059 | 73.13 | 97.49 | 57.55 | 53.31 | 0.0016 | 0.0000 | 2298 |
| Bagging_DecisionStump | 0.8402 | 0.7059 | 73.16 | 97.55 | 57.57 | 53.34 | 0.0148 | 0.0000 | 4418 |

The example training and testing times for each model, and the model size is listed. Since the predictor module 104 can perform a 10-fold cross-validation, training time is on 90% of the data, testing time is on 10% of the data, and model size also corresponds to the model build on 90% of the data (averaged across a determined number of runs, e.g., 100 runs). In some examples, the predictor module 104 can use Waikato Environment for Knowledge Analysis (WEKA) data mining software version 3.7.13 for analytics with default parameters, unless otherwise stated. The example results were obtained by using the entire set of input attributes. Table 1 is sorted by the MAE metric, and the performance numbers that are not statistically distinguishable at p=0.05 are boldfaced. The top four models from Table 1 are subsequently combined using the Voting modeling scheme to obtain the final model ($R^2$=0.9819, MAE=17.67 MPa, RMSE=25.08 MPa), whose performance is found to be better than all the four constituent models, as well as better than the modeling techniques used previously in A. Agrawal, P. D. Deshpande, A. Cecen, G. P. Basavarsu, A. N. Choudhary, S. R. Kalidindi, "Exploration of data science techniques to predict fatigue strength of steel from composition and processing parameters," Integrating Materials and Manufacturing Innovation 3 (8), 2014, pp. 1-19, at p=0.05.

Figure 3A:
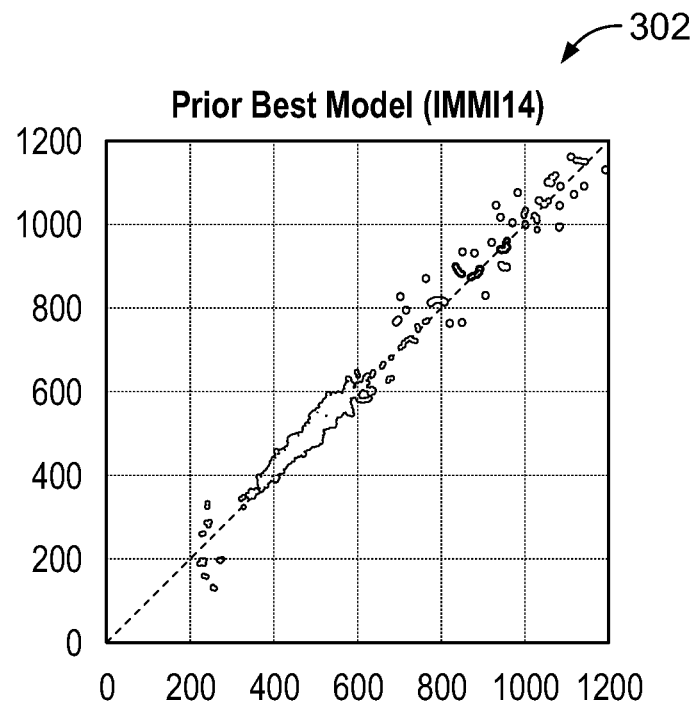
FIGS. 3A and 3B are graphs of example scatter plots comparing a best model from a previous model with a new model based on a Voting scheme.
Figure 3B:
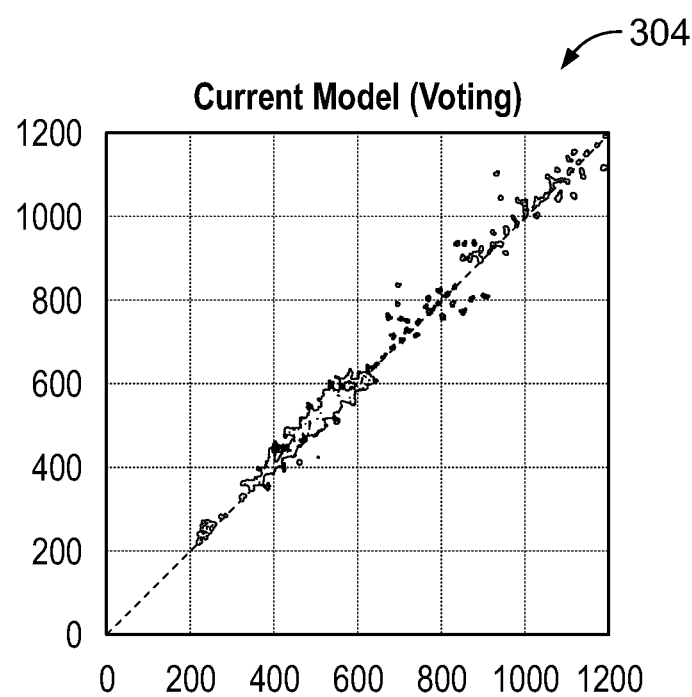
Figure 4A:
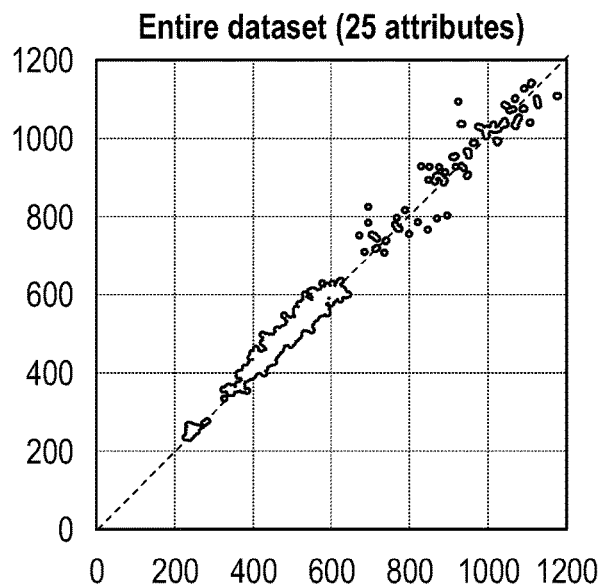
FIGS. 4A-D are graphs that show example scatter plots.
Figure 4B:
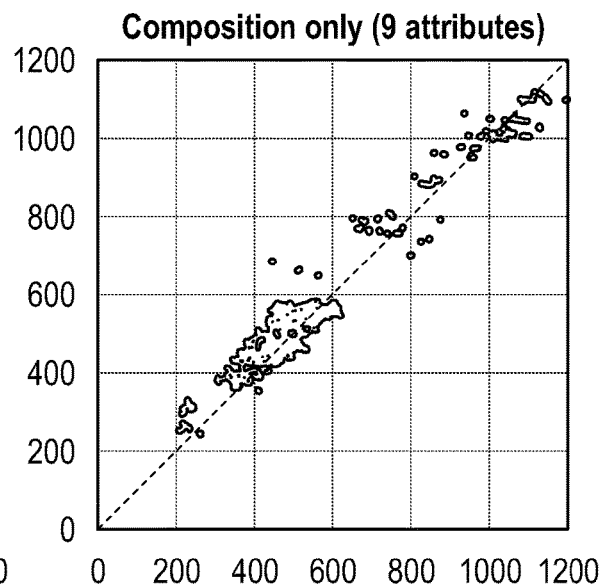
Figure 4C:
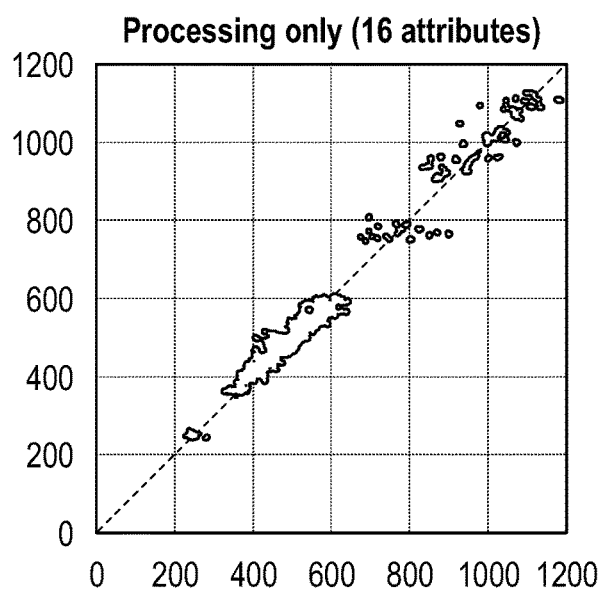
Figure 4D:
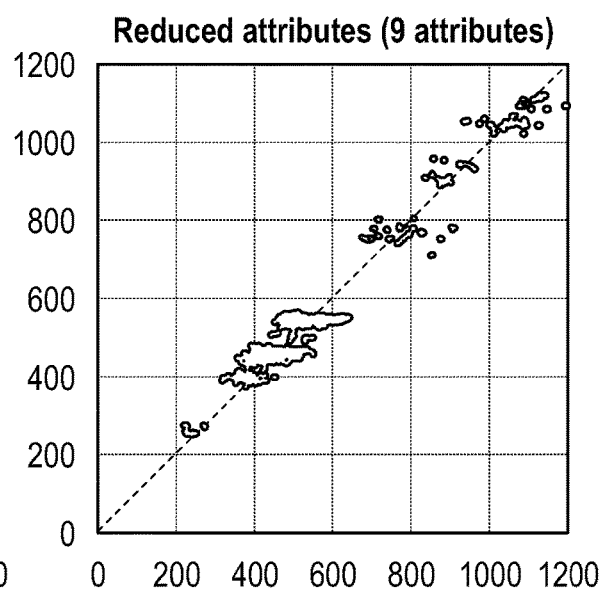
Figure 5A:
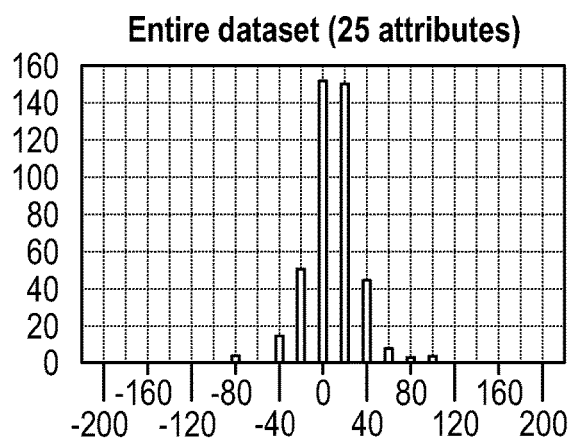
FIGS. 5A-D are graphs that show example error histograms.
Figure 5B:
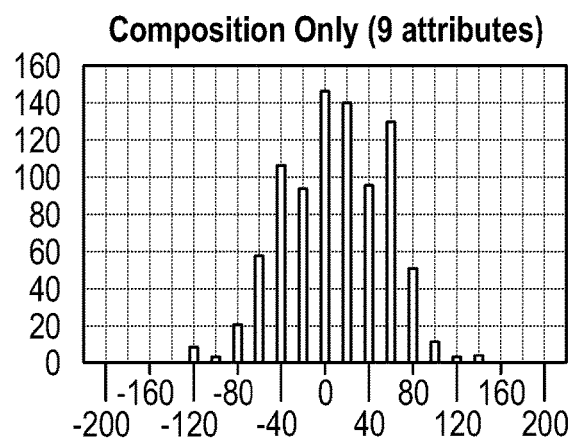
Figure 5C:
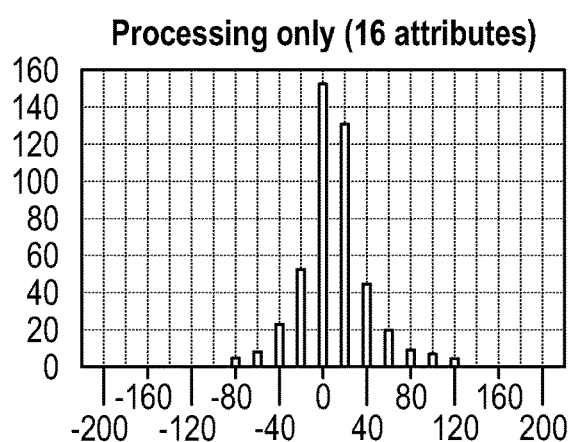
Figure 5D:
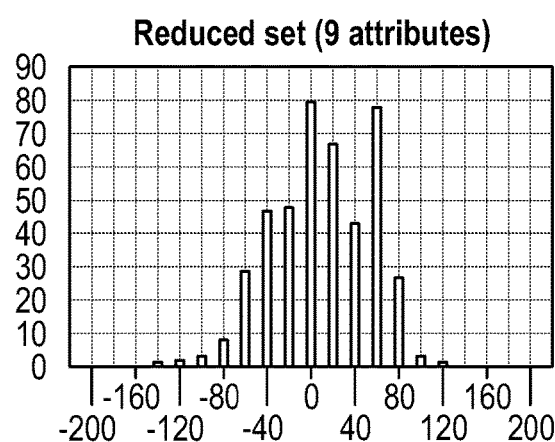

FIGS. 3A and 3B are graphs of example scatter plots comparing a best model 302 from A. Agrawal with a new model 304 based on the Voting scheme. The Voting scheme model can perform better in the low fatigue strength region of the plot where the A. Agrawal fails. Visual inspection of the scatter plots FIGS. 3A and 3B also reveal that the predictor module 104 model is able to make more accurate predictions for carbon and low alloy steels, where the best model in A. Agrawal had failed.

Since the NIMS dataset can provide composition and processing attributes, additional examples can be performed with composition attributes (9) and processing attributes (16). The same setting of 10-fold cross-validation can be used, with 10 runs for statistical significance testing. Additive regression with M5 model trees as underlying regressor can be found to be the most accurate model for the composition-only dataset ($R^2$=0.9308, MAE=38.86 MPa, RMSE=48.14 MPa), and also better than other models, so a Voting scheme may not be necessary to combine multiple models. For the processing-only dataset, two models can result in statistically indistinguishable performance. One is RandomForest and the other is RandomCommittee with REPTree as the base regressor. Combining these two with Voting scheme can provide the following accuracy numbers: $R^2$=0.9738, MAE=21.63 MPa, RMSE=30.19 MPa. In these examples, neither composition attributes alone nor processing attributes alone perform as well as using both together, suggesting that they capture complimentary information about materials, and can contribute to model accuracy.

In another example, correlation feature selection (CFS) can be used to identify subsets of both kinds of composition and processing attributes. The predictor module 104 application of CFS technique to composition attributes can identify a subset of six composition attributes: C, Si, P, Cr, Cu and Mo. The same analysis on processing attributes can identify a subset of three processing attributes: THT (through hardening temperature), THQCr (cooling rate for through hardening), and Tt (tempering time). Combining these six composition and three processing attributes make a new dataset of nine attributes. The predictor module 104 can perform the regression modeling with various modeling schemes using the same settings (10 runs of 10-fold cross-validation) to obtain best predictive models for the example dataset. Table 2 presents an example comparison of different techniques with 10-fold cross-validation setting using reduced subset of 9 non-redundant attributes (table sorted by MAE, best accuracy numbers boldfaced that were statistically not distinguishable at p=0.05, modeling techniques used in the final Voting model also boldfaced). The top three models can be found to have statistically indistinguishable accuracy on all performance metrics, and are thus combined using the Voting scheme, resulting in the following accuracy numbers: $R^2$=0.9440, MAE=36.41 MPa, RMSE=44.14 MPa

TABLE 2

| Modeling Scheme | R | $R^2$ | MAE (MPa) | RMSE (MPa) | RAE (%) | RRSE (%) | TrainTime (s) | TestTime (s) | ModelSize (bytes) |
|---|---|---|---|---|---|---|---|---|---|
| RandomCommittee_REPTree | 0.9680 | 0.9370 | 37.36 | 45.74 | 29.57 | 25.04 | 0.0265 | 0.0001 | 46157 |
| RotationForest_MLP | 0.9679 | 0.9368 | 37.86 | 46.18 | 29.98 | 25.29 | 1.1262 | 0.0036 | 257569 |
| RotationForest_REPTree | 0.9673 | 0.9357 | 37.86 | 46.41 | 29.96 | 25.43 | 0.0671 | 0.0029 | 241800 |
| M5 ModelTrees | 0.9666 | 0.9343 | 38.25 | 46.85 | 30.24 | 25.63 | 0.0547 | 0.0001 | 14884 |
| AdditiveRegression_M5 | 0.9666 | 0.9343 | 38.25 | 46.85 | 30.24 | 25.63 | 0.1678 | 0.0002 | 26643 |
| Bagging_MLP | 0.9669 | 0.9349 | 38.44 | 46.92 | 30.42 | 25.68 | 1.0263 | 0.0005 | 70459 |
| Bagging_M5 | 0.9662 | 0.9335 | 38.52 | 47.17 | 30.46 | 25.82 | 0.4883 | 0.0005 | 115962 |

TABLE 2-continued

| Modeling Scheme | R | R² | MAE (MPa) | RMSE (MPa) | RAE (%) | RRSE (%) | TrainTime (s) | TestTime (s) | ModelSize (bytes) |
|---|---|---|---|---|---|---|---|---|---|
| RotationForest_M5 | 0.9667 | 0.9345 | 38.53 | 47.08 | 30.45 | 25.75 | 0.5809 | 0.0033 | 300707 |
| Bagging_REPTree | 0.9661 | 0.9333 | 38.71 | 47.16 | 30.65 | 25.83 | 0.0251 | 0.0001 | 69484 |
| NeuralNetworks (MLP) | 0.9659 | 0.9330 | 38.79 | 47.56 | 30.71 | 26.04 | 0.0997 | 0.0002 | 10070 |
| RandomCommittee_MLP | 0.9648 | 0.9308 | 39.24 | 48.34 | 31.09 | 26.48 | 1.0321 | 0.0005 | 70183 |
| REPTree | 0.9631 | 0.9276 | 39.26 | 48.83 | 31.02 | 26.68 | 0.0026 | 0.0001 | 6370 |
| AdditiveRegression_REPTree | 0.9610 | 0.9235 | 39.66 | 50.01 | 31.28 | 27.23 | 0.0048 | 0.0001 | 7454 |
| RandomSubSpace_REPTree | 0.9615 | 0.9245 | 40.16 | 50.44 | 31.70 | 27.56 | 0.0186 | 0.0002 | 71785 |
| AdditiveRegression_MLP | 0.9622 | 0.9258 | 40.46 | 49.34 | 32.07 | 27.10 | 0.7933 | 0.0006 | 65278 |
| DecisionTable | 0.9551 | 0.9122 | 41.17 | 53.09 | 32.59 | 29.13 | 0.0123 | 0.0002 | 18154 |
| RandomSubSpace_M5 | 0.9599 | 0.9214 | 42.53 | 52.77 | 33.53 | 28.85 | 0.4339 | 0.0009 | 130728 |
| SVM | 0.9528 | 0.9078 | 43.85 | 56.24 | 34.57 | 30.66 | 0.0881 | 0.0001 | 58672 |
| RotationForest_LinearRegression | 0.9540 | 0.9101 | 43.90 | 55.37 | 34.62 | 30.20 | 0.0526 | 0.0031 | 221755 |
| Bagging_LinearRegression | 0.9537 | 0.9095 | 43.98 | 55.58 | 34.68 | 30.31 | 0.0091 | 0.0002 | 30594 |
| RandomSubSpace_MLP | 0.9552 | 0.9124 | 44.07 | 55.21 | 34.72 | 30.15 | 0.6222 | 0.0008 | 79472 |
| LinearRegression | 0.9534 | 0.9090 | 44.11 | 55.76 | 34.79 | 30.41 | 0.0009 | 0.0001 | 5638 |
| AdditiveRegression_LinearRegression | 0.9534 | 0.9090 | 44.11 | 55.76 | 34.79 | 30.41 | 0.0029 | 0.0002 | 8955 |
| RandomForest | 0.9551 | 0.9122 | 44.36 | 53.68 | 35.15 | 29.46 | 0.2147 | 0.0024 | 1844181 |
| AdditiveRegression_DecisionStump | 0.9533 | 0.9088 | 44.43 | 55.12 | 35.07 | 30.20 | 0.0069 | 0.0001 | 3503 |
| Bagging_RandomTree | 0.9527 | 0.9076 | 45.76 | 55.07 | 36.28 | 30.21 | 0.0280 | 0.0002 | 182919 |
| RandomSubSpace_RandomTree | 0.9497 | 0.9019 | 46.96 | 56.83 | 37.23 | 31.20 | 0.0250 | 0.0006 | 214037 |
| NearestNeighbor_Kstar | 0.9481 | 0.8989 | 47.16 | 57.46 | 37.40 | 31.57 | 0.0002 | 0.0843 | 51433 |
| NearestNeighbor_Ibk | 0.9498 | 0.9021 | 47.24 | 56.94 | 37.47 | 31.26 | 0.0001 | 0.0020 | 45971 |
| RotationForest_RandomTree | 0.9489 | 0.9004 | 47.26 | 57.19 | 37.49 | 31.42 | 0.0754 | 0.0031 | 398752 |
| RandomCommittee_RandomTree | 0.9493 | 0.9012 | 47.31 | 57.11 | 37.53 | 31.37 | 0.0315 | 0.0003 | 205941 |
| AdditiveRegression_RandomTree | 0.9487 | 0.9000 | 47.42 | 57.46 | 37.61 | 31.55 | 0.0107 | 0.0001 | 29506 |
| RandomTree | 0.9474 | 0.8976 | 47.63 | 57.98 | 37.77 | 31.86 | 0.0031 | 0.0001 | 22236 |
| Gaussianrocess | 0.9145 | 0.8363 | 52.83 | 73.36 | 41.50 | 39.93 | 0.0804 | 0.0706 | 680172 |
| RandomSubSpace_LinearRegression | 0.9266 | 0.8586 | 56.35 | 75.39 | 44.09 | 40.80 | 0.0087 | 0.0004 | 42166 |
| RotationForest_DecisionStump | 0.8533 | 0.7281 | 71.49 | 94.09 | 56.22 | 51.40 | 0.0480 | 0.0027 | 198090 |
| DecisionStump | 0.8402 | 0.7059 | 73.13 | 97.49 | 57.55 | 53.31 | 0.0006 | 0.0000 | 1607 |
| Bagging_DecisionStump | 0.8397 | 0.7051 | 73.21 | 97.63 | 57.62 | 53.39 | 0.0062 | 0.0001 | 3727 |
| RandomSubSpace_DecisionStump | 0.8115 | 0.6585 | 76.10 | 104.92 | 59.79 | 57.24 | 0.0059 | 0.0002 | 18168 |

Table 3 lists example accuracy numbers of the final Voting models on different subsets of the NIMS database. FIGS. 4A-D and FIGS. 5A-D are graphs that show example scatter plots and error histograms, respectively, of the final Voting models for the four attribute sets.

TABLE 3

| Dataset | #Attributes | R | R² | MAE (MPa) | RMSE (MPa) | RAE (%) | RRSE (%) |
|---|---|---|---|---|---|---|---|
| Entire dataset | 25 | 0.9909 | 0.9819 | 17.67 | 25.08 | 13.79 | 13.43 |
| Composition only | 9 | 0.9648 | 0.9308 | 38.86 | 48.14 | 30.64 | 26.24 |
| Processing only | 16 | 0.9868 | 0.9738 | 21.63 | 30.19 | 16.87 | 16.18 |
| Reduced set | 9 | 0.9716 | 0.9440 | 36.41 | 44.14 | 28.40 | 23.65 |

Figure 6:
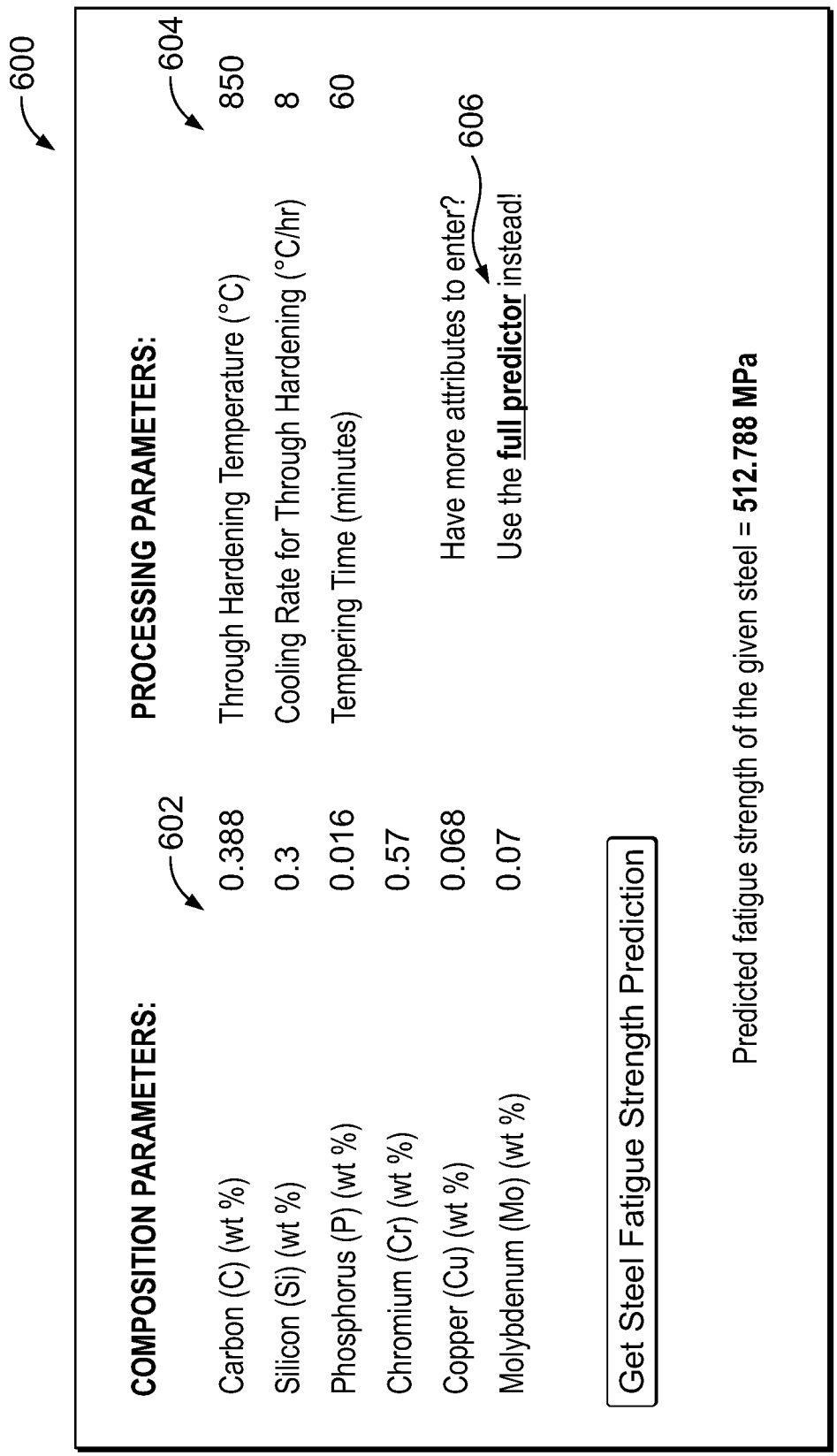
FIG. 6 is a screenshot of an example fatigue strength predictor input screen of the predictor module.

FIG. 6 is a screenshot of an example fatigue strength predictor input screen 600 of the predictor module 104. Most data-driven predictive models are, in general, not simple equations as in the case of something like linear regression, and are more like black box models that are not directly interpretable. This is even more the case with advanced ensembling techniques. Therefore, it is not straightforward to use these forward models in traditional spreadsheet software to get property predictions for a given material representation, and usually some code/scripts in an appropriate programming language, depending on how the models were created in the first place, are needed to use such models and make predictions.

To make the predictive models readily accessible for use by the materials science and engineering community, the predictor module 104 can determine steel fatigue strength from inputted values 602, 604 of a reduced set of attributes, e.g., as described above. In some examples, the predictor module 104 generates predictions of fatigue strength for a steel. The reduced set of attributes 600 can be determined for the predictor module 104 so that the user device 102 does not have to enter too many attributes and still obtain a satisfactory accuracy, but the option of using a fuller predictor (700 in FIG. 7) with additional attributes 702, 704 is also possible, e.g., by clicking the full predictor link 606. The reduced set of composition parameters can include carbon, silicon, phosphorus, chromium, copper and molybdenum. The reduced set of processing parameters can include through hardening temperature, cooling rate for through hardening and tempering time. The final Voting models are deployed in the predictor module 104 for both the composition and processing attribute sets. An advantage of the predictor module 104 is ready access to fast and accurate forward models of PSPP relationships without the need to do experiments and simulations, which can help identify promising candidates for further exploration with simulations and/or experiments.

FIG. 7 is a screenshot of an example expanded fatigue strength predictor of the predictor module 104. The user device 102 can display additional attributes upon an input from the user, e.g., clicking the link 606 for the predictor module 104 to the display the expanded list. The expanded list of composition parameter can include carbon, silicon, manganese, phosphorus, Sulphur, nickel, chromium, copper, molybdenum, area proportion of inclusion deformed by plastic work, area proportion of inclusion occurring in discontinuous array and area proportion of isolated inclusions. The expanded list of processing parameters can include normalizing temperature, through hardening temperature, through hardening time, cooling rate for through hardening, carburization temperature, carburization time, diffusion temperature, diffusion time, quenching media temperature carburization, tempering temperature, tempering time, cooling rate for tempering and reduction ratio. Other attributes may be used, e.g., by using calculation of phase diagrams (CALPHAD) techniques and/or using data-driven modeling techniques to building and deploying accurate models for other material properties.

Figure 8A:
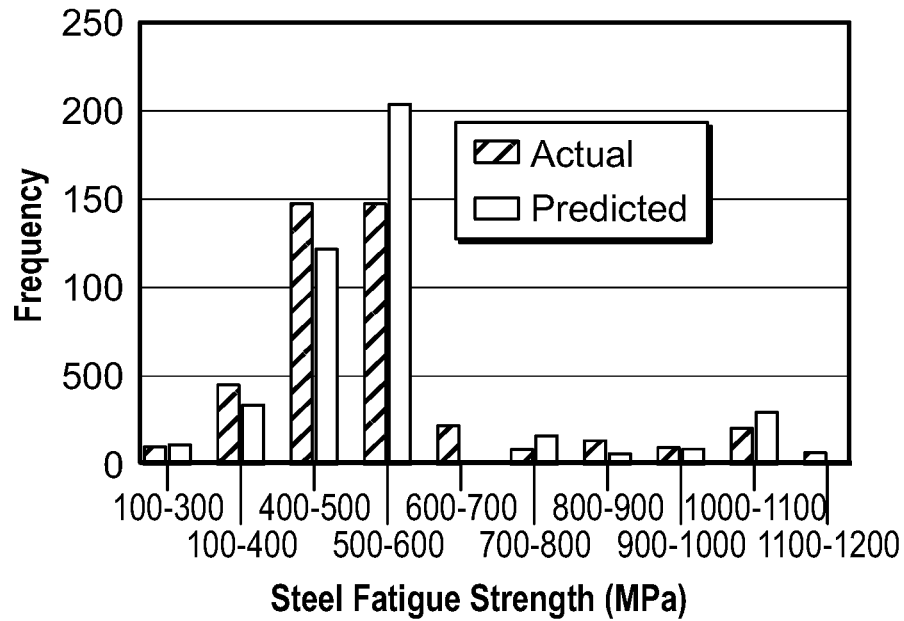
FIGS. 8A-8B are graphs of example histograms of steel fatigue strength data and prediction errors of the fatigue strength predictor of the predictor module.
Figure 8B:
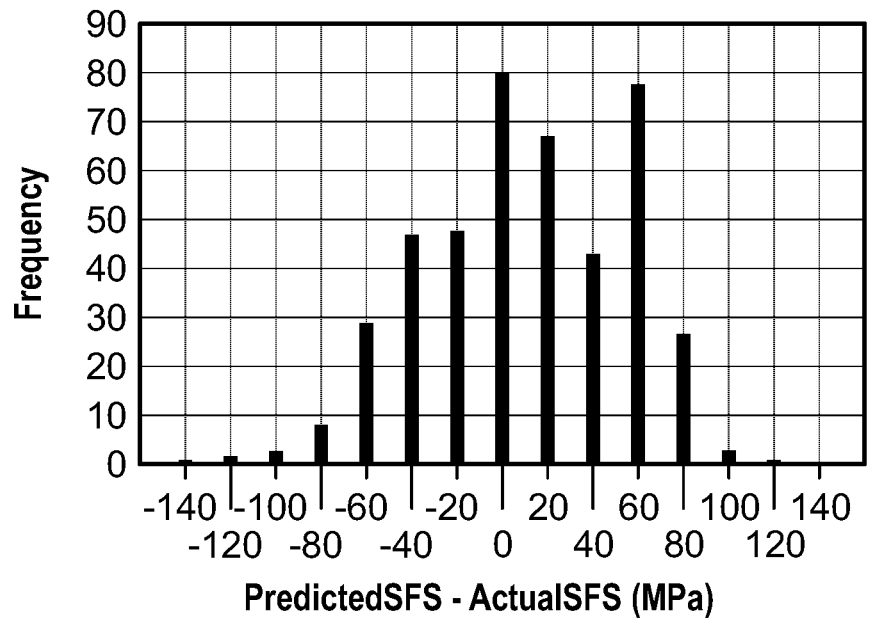

FIGS. 8A-8B are graphs of example histograms of steel fatigue strength data 802 and prediction errors 804 of the fatigue strength predictor of the predictor module 104, e.g., upon inputting of the data.

Figure 9:
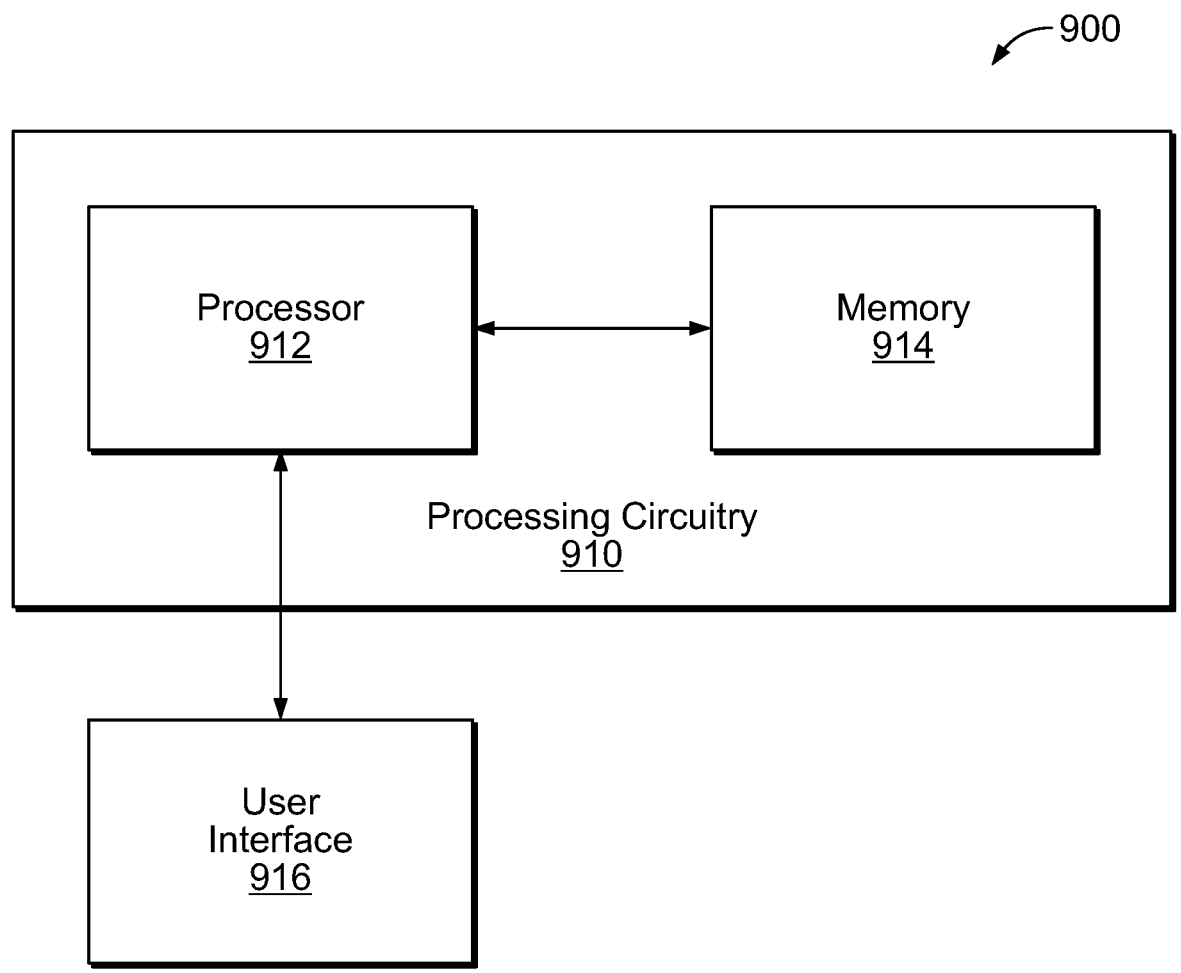
FIG. 9 is a block diagram of an example computing device for one or more the user devices and the predictor module.

FIG. 9 is a block diagram of an example computing device 900 for one or more the user devices 102 and the predictor module 104. The systems and methods described above may be implemented in many different ways in many different combinations of hardware, software firmware, or any combination thereof. In one example, the computing device 900 may be implemented in one or more of user devices 102 and the predictor module 104. It will be appreciated that the components, devices or elements illustrated in and described with respect to FIG. 9 below may not be mandatory and thus some may be omitted in certain embodiments. Additionally, some embodiments may include further or different components, devices or elements beyond those illustrated in and described with respect to FIG. 9.

In some example embodiments, the computing device 900 may include processing circuitry 910 that is configurable to perform actions in accordance with one or more example embodiments disclosed herein. In this regard, the processing circuitry 910 may be configured to predict strength of alloys based on received composition parameters and/or processing parameters. The processing circuitry 910 may be configured to perform data mining, data processing, application execution and/or other processing according to one or more examples. In some examples, the computing device 900 or a portion(s) or component(s) thereof, such as the processing circuitry 910, may include one or more chipsets and/or other components that may be provided by integrated circuits.

In some example embodiments, the processing circuitry 910 may include a processor 912 and, in some embodiments, such as that illustrated in FIG. 9, may further include memory 914. The processor 912 may be embodied in a variety of forms. For example, the processor 912 may be embodied as various hardware-based processing means such as a microprocessor, a coprocessor, a controller or various other computing or processing devices including integrated circuits such as, for example, an ASIC (application specific integrated circuit), an FPGA (field programmable gate array), some combination thereof, or the like. Although illustrated as a single processor, it will be appreciated that the processor 912 may comprise a plurality of processors. The plurality of processors may be in operative communication with each other and may be collectively configured to perform one or more functionalities of the computing device 900 as described herein. In some example embodiments, the processor 912 may be configured to execute instructions that may be stored in the memory 914 or that may be otherwise accessible to the processor 912. As such, whether configured by hardware or by a combination of hardware and software, the processor 912 is capable of performing operations according to various embodiments while configured accordingly.

In some example embodiments, the memory 914 may include one or more memory devices. Memory 914 may include fixed and/or removable memory devices. In some embodiments, the memory 914 may provide a non-transitory computer-readable storage medium that may store computer program instructions that may be executed by the processor 912. In this regard, the memory 914 may be configured to store information, data, applications, instructions and/or the like for enabling the computing device 900 to carry out various functions in accordance with one or more example embodiments. In some embodiments, the memory 914 may be in communication with one or more of the processor 912, the user interface 916 for passing information among components of the computing device 900.

While various embodiments have been described, it can be apparent that many more embodiments and implementations are possible. Accordingly, the embodiments are not to be restricted.

We claim:

1. A system, comprising:
a computer having a processor that executes predictor algorithm program code stored in a non-transitory computer-readable memory to process input parameters received via a network, to predict a material property of an alloy based on the input parameters, wherein the predictor algorithm is based on a plurality of predictive models, and the input parameters for each of the plurality of predictive models are selected from one or a combination of a reduced set of composition parameters and an expanded list of composition parameters, wherein the reduced set of composition parameters comprises amount of carbon, amount of silicon, amount of phosphorus, amount of chromium, amount of copper and amount of molybdenum, wherein the expanded list of composition parameters comprises amount of manganese, amount of sulphur, amount of nickel, area proportion of inclusion deformed by plastic work, area proportion of inclusion occurring in discontinuous array and area proportion of isolated inclusions;

the processor configured to output a predicted field strength of the alloy for each of the plurality of predictive models according to a ranking, and to display a best average value of the predicted field strength of the alloy from a subset of the highest ranked predictive models.

2. The system of claim 1, wherein the input parameters are further selected from a reduced set of processing parameters, wherein the reduced set of processing parameters comprise a through hardening temperature, a cooling rate for through hardening and a tempering time.

3. The system of claim 2, wherein the input parameters are further selected from an expanded list of processing parameters, wherein the expanded list of processing parameters comprise a normalizing temperature, a through hardening time, a carburization temperature, a carburization time, a diffusion temperature, a diffusion time, a quenching media temperature carburization, a tempering temperature, a cooling rate for tempering and a reduction ratio.

4. The system of claim 1, where the alloy comprises steel.

5. The system of claim 1, where the material property comprises a field strength.

6. The system of claim 1, where the predictor algorithm is configured to build the predictive model based on data mining a database.

7. A computer-implemented method, comprising:

executing by a processor in a computer, predictor algorithm program code stored in a non-transitory computer-readable memory, wherein the processor is configured to process input parameters received via a network, to predict a field strength of an alloy based on the input parameters, wherein the predictor algorithm is based on a plurality of predictive models, and the input parameters for each of the plurality of predictive models are selected from one or a combination of a reduced set of composition parameters and an expanded list of composition parameters, wherein the reduced set of composition parameters comprises amount of carbon, amount of silicon, amount of phosphorus, amount of chromium, amount of copper and amount of molybdenum, wherein the expanded list of composition parameters comprises amount of manganese, amount of sulphur, amount of nickel, area proportion of inclusion deformed by plastic work, area proportion of inclusion occurring in discontinuous array and area proportion of isolated inclusions; and outputting by the processor, the predicted field strength of the alloy for each of the plurality of predictive models according to a ranking, and to display a best average value of the predicted field strength of the alloy from a subset of the highest ranked predictive models.

8. The method of claim 7, wherein the input parameters are further selected from a reduced set of processing parameters, wherein the reduced set of processing parameters comprise a through hardening temperature, a cooling rate for through hardening and a tempering time.

9. The method of claim 8, wherein the input parameters are further selected from an expanded list of processing parameters, wherein the expanded list of processing parameters comprise a normalizing temperature, a through hardening time, a carburization temperature, a carburization time, a diffusion temperature, a diffusion time, a quenching media temperature carburization, a tempering temperature, a cooling rate for tempering and a reduction ratio.

10. The method of claim 7, where the alloy comprises steel.

11. The method of claim 7, where the field strength comprises fatigue strength.

12. The method of claim 7, further comprising building the predictive model based on data mining a database.

* * * * *